US010172872B2

(12) United States Patent
Gaihede

(10) Patent No.: US 10,172,872 B2
(45) Date of Patent: Jan. 8, 2019

(54) TREATMENT OF OTITIS MEDIA WITH RETROAURICULAR INJECTION OF AN ANTI-INFLAMMATORY DRUG

(71) Applicant: Region Nordjylland, Aalborg Universitetshospital, Aalborg (DK)

(72) Inventor: Michael Lyhne Gaihede, Aalborg (DK)

(73) Assignee: REGION NORDJYLLAND AALBORG UNIVERSITETHOSPITAL, Aalborg (CH)

( * ) Notice: Subject to any disclaimer, the term of this patent is extended or adjusted under 35 U.S.C. 154(b) by 0 days.

(21) Appl. No.: 15/737,427

(22) PCT Filed: Jun. 30, 2016

(86) PCT No.: PCT/DK2016/050229
§ 371 (c)(1),
(2) Date: Dec. 18, 2017

(87) PCT Pub. No.: WO2017/000966
PCT Pub. Date: Jan. 5, 2017

(65) Prior Publication Data
US 2018/0169116 A1    Jun. 21, 2018

(30) Foreign Application Priority Data
Jul. 1, 2015  (DK) .................................. 2015 70424

(51) Int. Cl.
*A61K 31/58* (2006.01)
*A61K 31/56* (2006.01)
*A61P 27/16* (2006.01)
*A61K 9/00* (2006.01)
*A61K 31/573* (2006.01)
*A61K 45/06* (2006.01)

(52) U.S. Cl.
CPC ............ *A61K 31/58* (2013.01); *A61K 9/0046* (2013.01); *A61K 9/0053* (2013.01); *A61K 31/56* (2013.01); *A61K 31/573* (2013.01); *A61K 45/06* (2013.01); *A61P 27/16* (2018.01)

(58) Field of Classification Search
None
See application file for complete search history.

(56) References Cited

U.S. PATENT DOCUMENTS 5,245,098 A    9/1993  Summers et al.
2013/0189241 A1  7/2013  O'Malley et al.

FOREIGN PATENT DOCUMENTS

WO  2005013936 A2    2/2005
WO  2006099325    *  9/2006
WO  2006099325 A2    9/2006

OTHER PUBLICATIONS

Varsano et al., Eur J Pediatr (1997) 156: 858-863 (Year: 1997).*
(Continued)

*Primary Examiner* — Karl J Puttlitz
(74) *Attorney, Agent, or Firm* — Dinsmore and Shohl, LLP

(57) ABSTRACT

The present invention relates to the treatment of otitis media, in particularly secretory otitis media, with an anti-inflammatory drug such as a steroid or a non-steroid anti-inflammatory drug, wherein said anti-inflammatory drug is formulated as a depot formulation for retroauricular injection.

9 Claims, 3 Drawing Sheets

(56) References Cited

OTHER PUBLICATIONS

International Search Report & Written Opinion for corresponding PCT/DK2016/050229, dated Sep. 27, 2016.
Chin-Lung Kuo et al, "New Therapeutic Strategy for Treating Otitis Media with Effusion in Postirradiated Nasopharyngeal Carcinoma Patients," Journal of the Chinese Medical Association, Elsevier (Singapore) PTE Ltd. Hong Kong Branch, Hong Kong, vol. 75, No. 7, Feb. 22, 2012, pp. 329-334.
Hausdorf, Experienced improved ejection fractoin or NYHA heart failure class after protected PCI procedure with the Impella Heart Pump; J Interv Cardiol. Feb. 14, 2001(1): 69-76.
Langer, Controlled Release of Macromolecules; Chem. Tech. 12:98-105; 1982.
Langer et al, Biocompatibility of polymeric delivery systems for macromolecules; J. Biomed. Mater. Res. 15: 167-277; 1981.
Sidman et al, Controlled release of macromolecules and pharmaceuticals from synthetic polypeptides based on glutamic acid; Biopolymers 22: 547-556; 1983.

* cited by examiner

TREATMENT OF OTITIS MEDIA WITH RETROAURICULAR INJECTION OF AN ANTI-INFLAMMATORY DRUG

FIELD OF INVENTION

The present invention relates to the treatment of otitis media with injections of anti-inflammatory drugs, in particularly depot injections, as well as a unit dose suitable for use in the treatment.

BACKGROUND OF INVENTION

Otitis Media

Otitis media (OM) is found in two main forms: 1) acute otitis media=AOM, and 2) secretory otitis media=SOM. If AOM is essentially conditioned by infection with airways bacteria, SOM is predominantly an inflammatory disease, where pathological bacteria are not usually found. The signs of SOM are quieter compared with AOM with an unpleasant pressure sensation in the ear and accumulation of effusion in the middle ear (ME) cavity with decreased hearing (30-40 dB HL). The disease mechanism is not fully known, but the fluid is traditionally considered a transudate due to formation of underpressure in the ME cavity. The treatment of SOM consists of insertion of a ventilation tube (VT) in the tympanic membrane (TM), which equilibrates the underpressure and drains the fluid, so that symptoms of hearing loss and pressure sensation are relieved.

The occurrence of SOM is very high, and it is considered the most frequent childhood disease after common cold. 90% of children will have experienced at least one episode of SOM before the age of 3-4 years. Similarly, the treatment with VT's is also very frequent, and 30% of children born in Denmark will have at least one episode of VT insertion before the age of 10 years. Further, it is not unusual that these children experience repeated VT insertions; among those primarily treated with VT's, another 40% will have a second VT, while another 40% of these will have a third VT. SOM is also described in older children as well as in adults, but with lower incidences; in practice, the high treatment numbers with VT are mostly in younger children with a peak incidence between 2-4 years old.

The high frequency of SOM treatment is related to high costs for the health authorities and also a number of complications. In Denmark, the insertion of VT's is performed in ENT special practices and represents around 10% of medical insurance costs for ENT practice; in other countries VT are performed in hospitals (for instance Sweden). Further, the intervention is made under a short anaesthesia in children, thus there are additional insurance costs related to this part; however, in adults, it may be performed under local anaesthesia.

Complications related to VT insertions include short-term AOM episodes with infection and purulent discharge from the ear with demand of ENT-specialist visits and topical treatment with antibiotic ear drops, as well as long term complications of permanent TM perforation in 2-5% of cases. This is mostly encountered in children with repeated VT insertions, and these complications require hospital admission with surgical reconstruction of the tympanic membrane (myringoplasty DCD00 and tympanoplasty DCD10).

Surgical Versus Medical Treatment

Whereas VT insertion is a surgical treatment, drug treatment of SOM has also been discussed and investigated with no success. For instance, cortico-steroids (here after referred to as steroids) have been used with or without the combination of antibiotics. The primary reason seems to be that the treatment with steroids is only possible with systemic administration, which may have serious side effects including decreased growth in children.

Thus, there exists a need for an effective yet less invasive treatment of otitis media.

SUMMARY OF INVENTION

The present inventor has found that otitis media, in particularly secretory otitis media, may be treated by a retroauricular administration of a depot formulation of an anti-inflammatory drug, for example a steroid or an NSAID. Accordingly, in a first aspect the invention relates to an anti-inflammatory drug such as a steroid or an NSAID for use in the treatment of otitis media in an individual, wherein said drug is formulated as a depot formulation to be administered as a subcutaneous injection. Thereby an effective treatment is provided without giving rise to systemic side effects of the anti-inflammatory agent. Also provided is a method of treatment or prophylaxis of otitis media in an individual in need thereof, comprising the step of retroauricular injection of a depot formulation of an anti-inflammatory drug.

The invention in another aspect also relates to a method of manufacturing a depot formulation of an anti-inflammatory drug, wherein said depot formulation is for retroauricular injection.

The depot formulation is administered to the mastoid, preferably through a retro-auricular subcutaneous injection, and due to the relatively tightly bound tissue it is preferred to use a small volume of the depot formulation. Accordingly, in another aspect the invention relates to a unit dose comprising 0.1-2.0 mL of said anti-inflammatory drug defined above, and for the use thereof in a method of treatment or prophylaxis of otitis media in an individual.

DETAILED DESCRIPTION OF THE INVENTION

The Structure of ME

Figure 1:
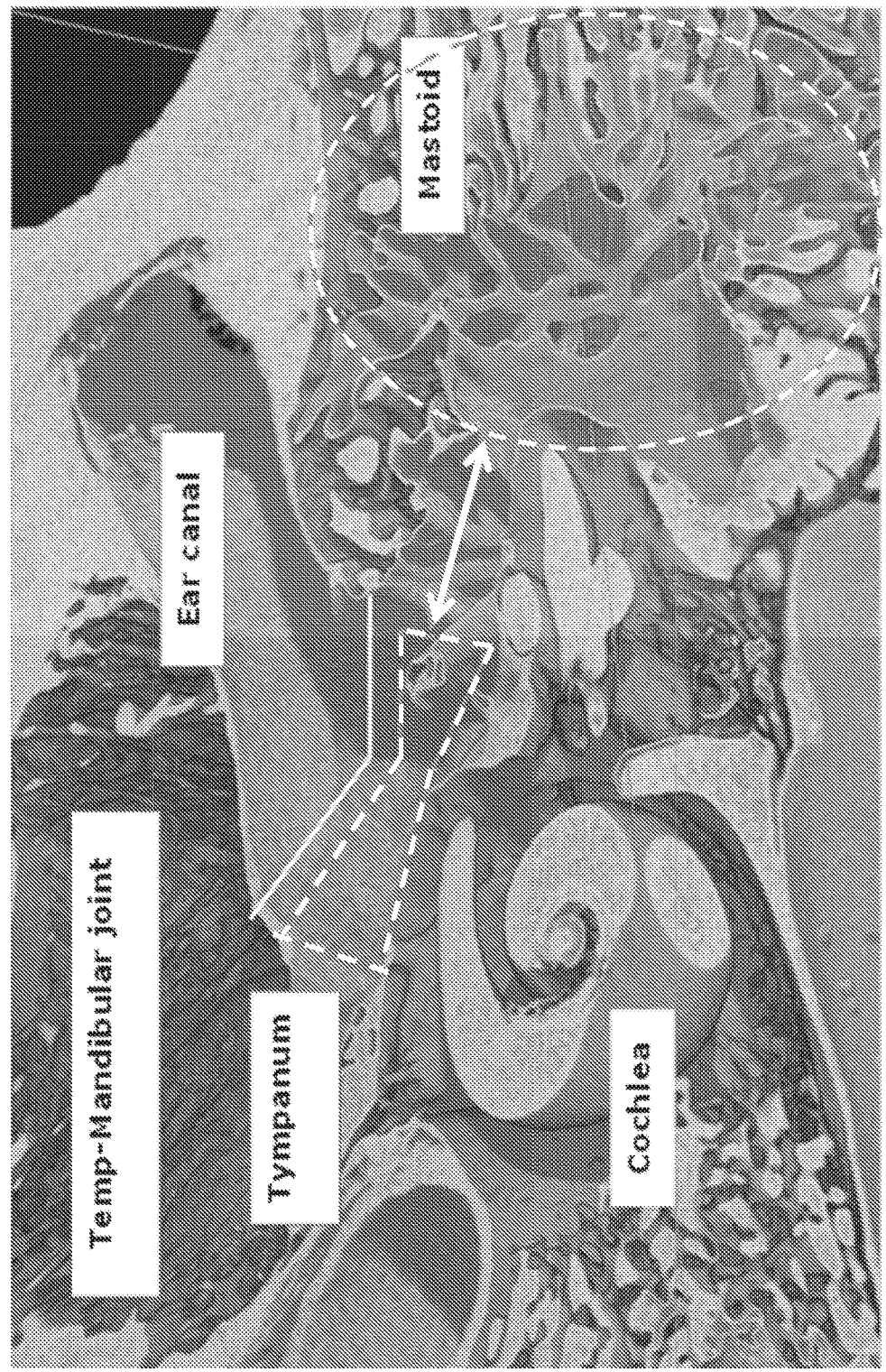
FIG. 1. The tympanum and the mastoid. The white full lines illustrate the tympanic membrane, which separates the ear canal from the tympanum; the tympanum is smaller and has smooth walls; by contrast the mastoid representing the largest part of the ME and it displays a branching structure with numerous divisions into smaller air cells formed by multiple thin bony septae.

The ME consists anatomically of 1) the tympanic cavity (tympanum), and 2) the mastoid. The tympanum is the part behind the TM, which contains the three ossicles (malleus, incus and stapes)—these structures including the TM are essential for sound transfer from the outer to the inner ear. The tympanum and the mastoid are connected by the antrum (FIG. 1: the double arrow) and they have volumes of respectively 1 and 6-10 $cm^3$. The mastoid has a particular cellular structure with numerous thin bony walls, which divide its volume into numerous air filled spaces (cells), and which causes a huge surface area relative to its volume (FIG. 1).

Both parts of the ME are covered by a mucosa layer, which is different in the two parts. In the tympanum, the mucosa is ciliated and has mucous producing goblet and glandular cells similar to airway epithelium; the submucosal connective tissue is dense. Thus, the tympanum mucosa is adapted to defence against infections with mucous production and a ciliary transport system of mucous towards the Eustachian tube. In the mastoid, the mucosa is thinner with a rich blood supply and a looser submucosal connective tissue. Thus, the mastoid mucosa lacks defence mechanisms, but its looser connective tissue and rich vascular structures may be very important related to a function, where changes in its congestion are essential for the overall ME physiology (see below).

The Development of the Mastoid

The development of the mastoid is very important for the understanding and the development of a series of ME diseases. While the tympanum is fully developed and aerated at birth, the mastoid has not been formed yet. This happens by a process called pneumatisation, where mesenchymal tissue behind the tympanum is gradually displaced by a formation and sequential expansion of air filled cells together with a simultaneous growth of the skull. Thus, it can be assumed that the mucosa and its blood supply will gradually expand similarly from the tympanum towards the mastoid air cells. The normal mastoid is fully developed only at pubertal age of 14-16 years old.

The present inventor has found that there is a direct blood supply to the mastoid mucosa from the retro-auricular area, which is a way to reach the ME with drugs that are injected subcutaneously. The advantage of this approach is that it has a stronger local effect and it ensures an access to the mastoid, which represents the largest part of the ME. Because the effect if predominantly local, the systemic effects are limited.

The otitis media treated according with the invention is any otitis media treatable with an anti-inflammatory drug. In some embodiments, as detailed below, the drug is a steroid. In other embodiments, the drug is an NSAID.

In preferred embodiments the otitis media is secretory otitis media (or suppurative otitis media).

The treatment is suitable for any individual, children or adults, however in a preferred embodiment the individual is a child, such as a child below 10 years of age, and more typically a child below 6 years of age.

Furthermore, the treatment may be used for prevention also, in particularly in individuals suffering from recurrent otitis media.

Anti-Inflammatory Drug

The depot formulation of the present invention enables administration of an anti-inflammatory drug. In particular, the anti-inflammatory drug is useful for treatment of otitis media. The term treatment herein refers also to prevention of otitis media in an individual suffering from recurrent otitis media, i.e. the treatment may also occur during asymptomatic periods.

The anti-inflammatory drug may be a steroidal anti-inflammatory agent, or a non-steroidal anti-inflammatory drug (NSAID), as detailed below.

The depot formulation may also comprise an amount of an anti-inflammatory drug formulation with a fast release, whereby the treatment both comprises a fast and a slow release ingredients.

Steroids

The steroid is any suitable steroid, such as a corticosteroid. In a preferred embodiment the steroid is a glucocorticosteroid.

For the depot formulation the glucocorticosteroid is preferably a glucocorticoid ester. Commercially available depot formulations are known in relation to treatment of joint disorders, such as betamethasone acetate, methylprednisolone, triamcinolonacetonide, and triamcinolonhexacetonide, and these depot formulations are useful in the present invention.

Examples of steroidal anti-inflammatory agents relevant for the present disclosure include but are not limited to hydrocortisone, cortisol, hydroxyltriamcinolone, alpha-methyl dexamethasone, dexamethasone-phosphate, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluocinolone acetonide, fluocinonide, flucortine butylesters, fluocortolone, fluprednidene(fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluocinolone, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, and triamcinolone.

In a preferred embodiment, the depot formulation used in the methods of treatment or prophylaxis disclosed herein comprises betamethasone. In another embodiment, the depot formulation comprises methylprednisolone. In another embodiment, the depot formulation comprises triamcinolonacetonide. In another embodiment, the depot formulation comprises triamcinolonhexacetonide.

The depot formulation may also comprise an amount of a steroid formulation with a fast release, whereby the treatment both comprises a fast and a slow release ingredients.

The steroid may be formulated in any conventional way in relation to formulation of liquid medicaments, such as the commercially available steroid depot formulations discussed above.

Non-Steroidal Anti-Inflammatory Drugs (NSAID)

In some embodiments, the depot formulations used in the present methods include an anti-inflammatory drug which is non-steroidal.

Non-limiting examples of non-steroidal anti-inflammatory compounds include acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, ketorolac, sulfasalazine, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Depot

A depot injection is an injection, usually subcutaneous, intradermal, or intramuscular, that deposits a drug in a localized mass, called a depot, from which it is gradually absorbed by surrounding tissue. Such injection allows the active compound to be released in a consistent way over a long period. Depot injections are typically either solid or oil-based.

The depot formulation disclosed herein comprises an anti-inflammatory drug. The depot may be made from polymers; biodegradable (also referred to as "resorbable" polymers) and/or non-biodegradable polymers can be used. These polymers are useful because of their versatile degradation kinetics, safety, and biocompatibility profiles. The polymers can be manipulated to modify the pharmacokinetics of the least one pharmaceutical agent contained within the depot, to shield the pharmaceutical agent from enzymatic attack, as well as degrade over time at the site of attachment such that the anti-inflammatory agent is released over time.

Natural biodegradable polymers include, but are not limited to, proteins (e.g. collagen, albumin, elastin, silk, glycosaminoglycans, chondroitin sulfate, or gelatin); polysaccharides (e.g., cellulose, cellulose starch, starch, alginates, chitin, chitosan, cyclodextrins, polydextrose, dextrans, glucosamine, hyaluronic acid, or hyaluronic acid esters) and lipids.

Examples of resorbable polymers include, but are not limited to, poly(alpha-hydroxy acids), poly(lactide-co-glycolide) (PLGA), polylactide (PLA), polyglycolide (PLG), polyethylene glycol (PEG), PEG conjugates of poly(α-hydroxy acids), polyorthoesters, polyaspirins, polyphosphazenes, vinylpyrrolidone, polyvinyl alcohol (PVA), PVA-g-PLGA, polyethylene glycol-terephthalate and polybutylene-terephthalate (PEGT-PBT) copolymer (polyactive), methacrylates, poly(N-isopropylacrylamide), polyethylene oxides (as known as polyoxyethylene or PEO), poly-propylene oxide (also known as polyoxypropylene or PPO), poly(aspartic acid) (PAA), PEO-PPO-PEO (Pluronics®, BASF), PEO-PPO-PAA copolymers, PLGA-PEO-PLGA, polyphosphoesters, polyanhydrides, polyester-anhydrides, polyamine acids, polyurethane-esters, polyphosphazines, polycaprolactones, polytrimethylene carbonates, polydioxanones, polyimide-esters, polyketals, polyacetals, polyethylene-vinyl acetates, silicones, polyurethanes, polypropylene fumarates, polydesaminotyrosine carbonates, polydesaminotyrosine arylates, polydesaminotyrosine ester carbonates, polydesaminotyrosine ester arylates, polyorthocarbonates, polycarbonates, or copolymers or physical blends thereof or combinations thereof.

More examples of synthetic biodegradable polymers include, but are not limited to, various polyesters, copolymers of L-glutamic acid and gamma ethyl-L-glutamate (Sidman et al., 1983, Biopolymers 22:547-556), polyphosphagenes, various hydrogels (see, for example, Langer et al., 1981, J. Biomed. Mater. Res, 15:167-277; Langer, 1982, Chem. Tech. 12:98-105), and poly-D-(−)-3-hydroxybutyric acid. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Atridox (PLA; periodontal disease), Nutropin Depot (PLGA; with hGH), and the Trelstar Depot (PLGA; prostate cancer).

Other synthetic polymers include, but are not limited to, poly(ε-caprolactone), poly(3-hydroxybutyrate), poly(β-malic acid) and poly(dioxanone), polyanhydrides, polyurethane (see WO 2005/013936), polyamides, polyorthoesters, n-vinyl alcohol, polyethylene oxide/polyethylene terephthalate or Dacron®, polyphosphate, polyphosphonate, polydihydropyran, and polyacytal.

In various embodiments, the drug depot comprises poly (lactide-co-glycolide) (PLGA), polylactide (PLA), polyglycolide (PGA), D-lactide, D,L-lactide, L-lactide, D,L-lactide-ε-caprolactone, D,L-lactide-glycolide-ε-caprolactone, glycolide-caprolactone or a combination thereof.

Examples of non-biodegradable polymers include, but are not limited to, various cellulose derivatives (carboxymethyl cellulose, cellulose acetate, cellulose acetate propionate, ethyl cellulose, hydroxypropyl methyl cellulose, hydroxyalkyl methyl celluloses, and alkyl celluloses), silicon and silicon-based polymers (such as polydimethylsiloxane), polyethylene-co-(vinyl acetate), poloxamer, polyvinylpyrrolidone, poloxamine, polypropylene, polyimide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-α-chloro-p-xylene, polymethylpentene, polysulfone, non-degradable ethylene-vinyl acetate (e.g., ethylene vinyl acetate disks and poly(ethylene-co-vinyl acetate)), and other related biostable polymers.

Non-resorbable polymers can also include, but are not limited to, delrin, polyurethane, copolymers of silicone and polyurethane, polyolefins (such as polyisobutylene and polyisoprene), acrylamides (such as polyacrylic acid and poly(acrylonitrile-acrylic acid)), neoprene, nitrile, acrylates (such as polyacrylates, poly(2-hydroxy ethyl methacrylate), methyl methacrylate, 2-hydroxyethyl methacrylate, and copolymers of acrylates with N-vinyl pyrrolidone), N-vinyl lactams, polyacrylonitrile, glucomannan gel, vulcanized rubber and combinations thereof. Examples of polyurethanes include thermoplastic polyurethanes, aliphatic polyurethanes, segmented polyurethanes, hydrophilic polyurethanes, polyether-urethane, polycarbonate-urethane and silicone polyether-urethane. The vulcanized rubber described herein may be produced, for example, by a vulcanization process utilizing a copolymer produced as described, for example, in U.S. Pat. No. 5,245,098 to Summers et al. from 1-hexene and 5-methyl-1,4-hexadiene.

Other suitable non-resorbable material include, but are not limited to, lightly or highly cross-linked biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. Depending on the amount of crosslinking within the bioresorbable polymers, the degradation time of the polymer can be reduced, thus making the polymer, for the purpose of this invention, appear to be non-resorbable over the time frame of the use of the material for this invention.

The depot may also contain shape memory polymers so that the depot can be compressed or folded prior to and during insertion through the capsule member and then be able to uncompress or unfold after the depot is in place. For example, a multi-block copolymer of oligo(ε-caprolactone)diol and crystallizable oligo(ρ-dioxanone)diol can be used to create a shape memory polymer. This shape memory polymer features two block-building segments, a hard segment and a 'switching' segment, which are linked together in linear chains. The higher-temperature shape is the polymer's 'permanent' form, which it assumes after heating. One component, oligo(ε-caprolactone)dimethacrylate, furnishes the crystallizable "switching" segment that determines both the temporary and permanent shape of the polymer. By varying the amount of the comonomer, n-butyl acrylate, in the polymer network, the cross-link density can be adjusted. In this way, the mechanical strength and transition temperature of the polymers can be tailored such that it can be used in the present invention. The shape memory polymers can be generated such that they return to their original shape with the application of an external stimulus. The external stimulus can be temperature, an electric or magnetic field, light, or a change in pH.

In an alternative embodiment, the depot may have a frame that can fold and unfold so that the depot can be compressed into a smaller shape for insertion and then expanded once the depot is in place. Examples of such a frame include, for example, BioSTAR catheter and STARFlex occluder and septal repair implant (NMT Medical, Boston, Mass.). This is used for insertion of a closure (patch) over a septal defect in the heart. A frame for insertion of the patch could have self-centering microsprings made of memory alloy such as nitinol, but be retractable and attached by releasable, biodegradable attachments to the polymer. In one embodiment, the depot may be folded as a single umbrella comprised of a matt of electrospun, biodegradable woven fibers containing or coated with drug. Deployment of the folded, umbrella-like matt with attached microsprings to the inner synovial membrane could be similar to deployment of the STARFlex device (see Hanusdorf, 2001) but using e.g. a canula. In various embodiments, matts are deployed with the umbrella shaped depot. The matts may be created by electrospinning, which typically involves using an electrical charge to form a mat of fine fibers.

Additional Drug

Besides the anti-inflammatory drug as mentioned above, the depot formulation of the present disclosure may also comprise an additional drug. The additional drug may be a second anti-inflammatory drug, such as a steroid, for example a glucocorticoid, preferably a glucocorticoid ester as described herein, or an NSAID. The additional drug may also be an antibiotic.

In some embodiments, the depot formulation is of a steroid, for example a glucocorticoid, preferably a glucocorticoid ester, further comprising an NSAID. In one embodiment, the depot formulation is of betamethasone and further comprises an NSAID. In another embodiment, the depot formulation is of methylprednisolone and further comprises an NSAID. In yet another embodiment, the depot formulation is of triamcinolonacetonide and further comprises an NSAID. In yet another embodiment, the depot formulation is of triamcinolonhexacetonide and further comprises an NSAID. Examples of NSAID that can be comprised in the depot formulation in addition to the above-listed steroids include acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; a salicylate, such as aspirin, disalcid, benorylate, trilisate, safapryn, solprin, diflunisal, and fendosal; an acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, ketorolac, sulfasalazine, indopropfen, pirprofen, carprofen, oxaprozin, pranoprofen, miroprofen, tioxaprofen, suprofen, alminoprofen, and tiaprofenic; or pyrazoles, such as phenylbutazone, oxyphenbutazone, feprazone, azapropazone, and trimethazone.

In some embodiments, the depot formulation is of a steroid, for example a glucocorticoid, preferably a glucocorticoid ester, and further comprises an antibiotic. Examples of suitable antibiotics are amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, ampicillin, carbenicillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin or tinidazole.

Accordingly, in one embodiment, the depot formulation comprises betamethasone and further comprises an antibiotic selected from amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin and tinidazole.

In another embodiment, the depot formulation comprises methylprednisolone and further comprises an antibiotic selected from amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin and tinidazole.

In yet another embodiment, the depot formulation comprises triamcinolonacetonide and further comprises an antibiotic selected from amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin and tinidazole.

In yet another embodiment, the depot formulation comprises triamcinolonhexacetonide and further comprises an antibiotic selected from amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin and tinidazole.

In other embodiments, the depot formulation is of an NSAID, such as acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; a salicylate, such as aspirin, disalcid, benorylate, trilisate, safapryn, solprin, diflunisal, and fendosal; an acetic acid derivative, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; a fenamate, such as mefenamic, meclofenamic, flufenamic, niflumic, and tolfenamic acids; a propionic acid derivative, such as ibuprofen, naproxen, benoxaprofen, flurbiprofen, ketoprofen, fenoprofen, fenbufen, ketorolac, sulfasalazine, indopropfen, pirprofen, carprofen, oxaprozin, pranoprofen, miroprofen, tioxaprofen, suprofen, alminoprofen, and tiaprofenic; or a pyrazole, such as phenylbutazone, oxyphenbutazone, feprazone, azapropazone, and trimethazone, and further comprises an antibiotic such as amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxtetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin or tinidazole.

Volume Administered

The depot formulation is administered through a subcutaneous injection to the area above the mastoid, and in a preferred embodiment the injection is performed as a retroauricular injection, i.e. behind the diseased ear. In a preferred embodiment the depot formulation is injected into the retroauricular fold. From the subcutaneous depot the anti-inflammatory agent then enters the mastoid to have its effect in the mastoid and the other parts of the middle ear.

However, the skin and tissue behind the ear are normally relatively tightly bound, and do not offer much space for injections, in particularly if the injections are to be carried out without too much pain. Accordingly, the volume of the depot formulation administered is very small, and normally much smaller than other depot formulations administered for example in the treatment of joint disorders and diseases.

Normally the volume of the depot formulation is in the range of from 0.1 to 2.0 mL, such as in the range of from 0.2 to 1.0 mL, such as in the range of from 0.2 to 0.8 mL, such as in the range of from 0.3 to 0.6 mL. One preferred volume is 0.25 mL, and another preferred volume is 0.5 mL. As a general rule, the smaller the size of the ear to which the retroauricular injection is to be performed, the smaller the desired volume of the depot formulation should be.

Accordingly, herein is provided a depot formulation of a steroid, such as a glucocorticoid, preferably a glucocorticoid ester, having a volume in the range of from 0.1 to 2.0 mL, such as in the range of from 0.2 to 1.0 mL, such as in the range of from 0.2 to 0.8 mL, such as in the range of from 0.3 to 0.6 mL. In one embodiment, the volume of the steroid depot formulation is 0.25 mL. In another embodiment, the volume of the steroid depot formulation is 0.5 mL.

Herein is also provided a depot formulation of betamethasone, having a volume in the range of from 0.1 to 2.0 mL, such as in the range of from 0.2 to 1.0 mL, such as in the range of from 0.2 to 0.8 mL, such as in the range of from 0.3 to 0.6 mL. In one embodiment, the volume of the betamethasone depot formulation is 0.25 mL. In another embodiment, the volume of the betamethasone depot formulation is 0.5 mL.

Also disclosed is a depot formulation of methylprednisolone, having a volume in the range of from 0.1 to 2.0 mL, such as in the range of from 0.2 to 1.0 mL, such as in the range of from 0.2 to 0.8 mL, such as in the range of from 0.3 to 0.6 mL. In one embodiment, the volume of the methyl prednisolone depot formulation is 0.25 mL. In another embodiment, the volume of the methylprednisolone depot formulation is 0.5 mL.

Also disclosed is a depot formulation of triamcinolonacetonide, having a volume in the range of from 0.1 to 2.0 mL, such as in the range of from 0.2 to 1.0 mL, such as in the range of from 0.2 to 0.8 mL, such as in the range of from 0.3 to 0.6 mL. In one embodiment, the volume of the triamcinolonacetonide depot formulation is 0.25 mL. In another embodiment, the volume of the triamcinolonacetonide depot formulation is 0.5 mL.

Also disclosed herein is a depot formulation of triamcinolonhexacetonide, having a volume in the range of from 0.1 to 2.0 mL, such as in the range of from 0.2 to 1.0 mL, such as in the range of from 0.2 to 0.8 mL, such as in the range of from 0.3 to 0.6 mL. In one embodiment, the volume of the triamcinolonhexacetonide depot formulation is 0.25 mL. In another embodiment, the volume of the triamcinolonhexacetonide depot formulation is 0.5 mL.

In other embodiments is provided a depot formulation of an NSAID, having a volume in the range of from 0.1 to 2.0 mL, such as in the range of from 0.2 to 1.0 mL, such as in the range of from 0.2 to 0.8 mL, such as in the range of from 0.3 to 0.6 mL. In one embodiment, the volume of the NSAID depot formulation is 0.25 mL. In another embodiment, the volume of the NSAID depot formulation is 0.5 mL. Examples of suitable NSAIDs are acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; salicylates, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, ketorolac, sulfasalazine, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Dosages

The dosage of the anti-inflammatory drug to be administered is determined balancing the interest of having an effect for sufficient period of time while at the same time avoiding a systemic effect of the drug. At the same time, considerations regarding the desired volume of the depot formulation may be important.

In some embodiments, the effect of the injection lasts for at least 1 day, such as at least 2 days, such as at least 3 days, such as at least 4 days, such as at least 5 days, such as at least 6 days, such as at least 1 week, such as at least 2 weeks, such as at least 3 weeks, such as at least 4 weeks, such as at least 5 weeks, such as at least 6 weeks, such as at least 7 weeks, such as at least 8 weeks, such as at least 1 month, such as at least 2 months, such as at least 3 months, such as at least 4 months, such as at least 5 months, such as at least 6 months.

It is preferred that the effect of the injection lasts for at least 2 weeks, however for some patients it may be advantageous if the effect is at least 3 or 4 weeks.

For depot formulations comprising one of the steroids specified above, the administered dosages are preferably as follows.

In embodiments, where the anti-inflammatory drug is betamethasone, the drug is present in the depot formulation at a concentration in the range of 0.7 to 140 mg/mL, such as 0.8 to 100 mg/mL, such as 0.9 to 50 mg/mL, such as 1 to 35 mg/mL, such as 1.1 to 30 mg/mL, such as 1.2 to 28 mg/mL, such as 1.3 to 25 mg/mL, such as 1.4 to 22.5 mg/mL, such as 1.5 to 20 mg/mL, such as 1.6 to 17.5 mg/mL, such as 1.8 to 15 mg/mL, such as 2 to 14 mg/mL, such as 2.2 mg/mL to 13 mg/mL, such as 2.5 to 12 mg/mL, such as 2.8 to 11 mg/mL, such as 3 to 10 mg/mL, such as 4 to 9 mg/mL, such as 5 to 8 mg/mL, such as 6 to 7 mg/mL, such as 7 mg/mL. In some embodiments, the volume of the depot is 0.25 mL and the concentration of betamethasone is between 5.6 and 56 mg/mL, such as between 6 and 50 mg/mL, for example between 7 and 45 mg/mL, such as between 8 and 40 mg/mL, for example between 9 and 35 mg/mL, such as between 10 and 30 mg/mL, for example between 12 and 25 mg/mL, such as between 15 and 20 mg/mL. In other embodiments, the volume of the depot formulation is 0.5 mL and the concentration of betamethasone is between 2.8 and 28 mg/mL, such as between 3 and 25 mg/mL, for example between 4 and 20 mg/mL, such as between 5 and 15 mg/mL, for example between 6 and 10 mg/mL, such as between 7 and 9 mg/mL, for example 7 mg/mL or 8 mg/mL.

In other embodiments, the drug is methylprednisolone and is present in the depot formulation at a concentration in the range of 2 to 800 mg/mL, such as 2.1 to 400 mg/mL, such as 2.2 to 300 mg/mL, such as 2.4 to 275 mg/mL, such as 2.5 to 200 mg/mL, such as 2.7 to 150 mg/mL, such as 2.9 to 125 mg/mL, such as 3 to 110 mg/mL, such as 3.5 to 100 mg/mL, such as 4 to 90 mg/mL, such as 4.5 to 80 mg/mL, such as 5 to 75 mg/mL, such as 6 mg/mL to 70 mg/mL, such as 7 to 65 mg/mL, such as 8 to 60 mg/mL, such as 9 to 55 mg/mL, such as 8 to 50 mg/mL, such as 9 to 45 mg/mL, such as 10 to 40 mg/mL, such as 15 to 40 mg/mL, such as 20 to 40 mg/mL, such as 25 to 40 mg/mL, such as 30 to 40 mg/mL, such as 35 to 40 mg/mL, such as 40 mg/mL. In some embodiments, the volume is 0.25 mL and the concentration of methylprednisolone is between 16 and 320 mg/mL, such as between 17 and 300 mg/mL, for example between 18 and 275 mg/mL, such as between 19 and 250 mg/mL, for example between 20 and 225 mg/mL, such as between 25 and 200 mg/mL, for example between 30 and 175 mg/mL, such as between 40 and 150 mg/mL, for example between 50 and 125 mg/mL, such as between 75 and 100 mg/mL. In other embodiments, the volume is 0.5 mL and the concentration of methylprednisolone is between 8 and 160 mg/mL, such as between 9 and 140 mg/mL, for example between 10 and 120 mg/mL, such as between 15 and 100 mg/mL, for example between 20 and 90 mg/mL, such as between 30 and 80 mg/mL, for example between 40 and 70 mg/mL, for example between 50 and 60 mg/mL.

In other embodiments, the drug is triamcinolonacetonide and is present in the depot formulation at a concentration in the range of 5 to 800 mg/mL, such as 5.5 to 400 mg/mL, such as 6 to 300 mg/mL, such as 6.5 to 275 mg/mL, such as 7 to 200 mg/mL, such as 7.5 to 150 mg/mL, such as 8 to 125 mg/mL, such as 9 to 110 mg/mL, such as 10 to 100 mg/mL, such as 11 to 90 mg/mL, such as 12 to 80 mg/mL, such as 13 to 75 mg/mL, such as 14 mg/mL to 70 mg/mL, such as 15 to 65 mg/mL, such as 17.5 to 60 mg/mL, such as 20 to 55 mg/mL, such as 25 to 50 mg/mL, such as 30 to 45 mg/mL, such as 35 to 40 mg/mL, such as 40 mg/mL. In some embodiments, the volume is 0.25 mL and the concentration of triamcinolonacetonide is between 40 and 320 mg/mL, such as between 50 and 300 mg/mL, for example between 60 and 275 mg/mL, such as between 70 and 250 mg/mL, for example between 80 and 225 mg/mL, such as between 90 and 200 mg/mL, for example between 100 and 175 mg/mL, such as between 125 and 150 mg/mL. In other embodiments, the volume is 0.5 mL and the concentration of triamcinolonacetonide is between 20 and 160 mg/mL, such as between 30 and 140 mg/mL, for example between 40 and 120 mg/mL, such as between 50 and 100 mg/mL, for example between 60 and 80 mg/mL, such as 70 mg/mL.

In other embodiments, the drug is triamcinolonhexacetonide and is present in the depot formulation at a concentration in the range of 2.5 to 800 mg/mL, such as 3 to 400 mg/mL, such as 3.5 to 300 mg/mL, such as 4 to 275 mg/mL, such as 4.5 to 200 mg/mL, such as 5 to 150 mg/mL, such as 6 to 125 mg/mL, such as 7 to 110 mg/mL, such as 8 to 100 mg/mL, such as 9 to 90 mg/mL, such as 10 to 80 mg/mL, such as 12.5 to 75 mg/mL, such as 15 mg/mL to 70 mg/mL, such as 17.5 to 65 mg/mL, such as 20 to 60 mg/mL, such as 20 to 50 mg/mL, such as 20 to 40 mg/mL, such as 20 to 30 mg/mL, such as 20 to 25 mg/mL, such as 20 mg/mL. In some embodiments, the volume is 0.25 mL and the concentration of triamcinolonhexacetonide is between 20 and 160 mg/mL, such as between 30 and 140 mg/mL, for example between 40 and 120 mg/mL, such as between 50 and 100 mg/mL, for example between 60 and 80 mg/mL, such as 70 mg/mL. In other embodiments, the volume is 0.5 mL and the concentration of triamcinolonhexacetonide is between 10 and 80 mg/mL, such as between 15 and 75 mg/mL, for example between 20 and 70 mg/mL, such as between 25 and 65 mg/mL, for example between 30 and 60 mg/mL, such as between 35 and 55 mg/mL, for example between 40 and 50 mg/mL, such as 55 mg/mL.

The present anti-inflammatory drugs may be administered in dosages that are such that the drug is therapeutically active over the desired period of time.

In some embodiments, the drug is betamethasone and the dosage is between 1 and 10 mg, such as between 1.5 and 9 mg, such as between 2 and 8 mg, such as between 2.5 and 7 mg, such as between 3 and 6 mg, such as between 3.5 and 5 mg, such as 4 mg.

In other embodiments, the drug is methylprednisolone and the dosage is between 1 and 50 mg, such as between 5 and 40 mg, such as between 10 and 30 mg, such as between 15 and 25 mg, such as between 16 and 24 mg, such as between 17 and 23 mg, such as between 18 and 22 mg, such as between 19 and 21 mg, such as 20 mg.

In other embodiments, the drug is triamcinolonacetonide and the dosage is between 1 and 50 mg, such as between 5 and 40 mg, such as between 10 and 30 mg, such as between 15 and 25 mg, such as between 16 and 24 mg, such as between 17 and 23 mg, such as between 18 and 22 mg, such as between 19 and 21 mg, such as 20 mg.

In other embodiments, the drug is triamcinolonhexacetonide and the dosage is between 1 and 20 mg, such as between 1.5 and 19 mg, such as between 2 and 18 mg, such as between 3 and 17 mg, such as between 4 and 16 mg, such as between 5 and 15 mg, such as between 6 and 14 mg, such as between 7 and 13 mg, such as between 8 and 12 mg, such as between 9 and 11 mg, such as 10 mg.

For other steroids the dosages are calculated as equivalents of the above dosages.

Oral Administration

The methods for treating or preventing otitis media disclosed herein involve the use of a depot formulation for retroauricular injection, where the depot comprises an anti-inflammatory drug. In some cases, it may be desirable to combine the use of the depot described herein with oral administration of an anti-inflammatory drug. In some embodiments, the anti-inflammatory drug to be administered orally is a steroid, such as a glucocorticoid ester. In some embodiments, the anti-inflammatory drug administered orally is betamethasone, methylprednisolone, triamcinolonacetonide or triamcinolonhexacetonide.

In other embodiments, the anti-inflammatory drug to be administered orally is an NSAID, such as acetaminophen, paracetamol, nabumetone, celecoxib, etodolac, nimesulide, apasone, gold, oxicams, such as piroxicam, isoxicam, meloxicam, tenoxicam, sudoxicam, and CP-14,304; a salicylate, such as aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acemetacin, fentiazac, zomepirac, clindanac, oxepinac, felbinac, and ketorolac; a fenamate, such as mefenamic, meclofenamic, flufenamic, niflumic, and tolfenamic acids; a propionic acid derivative, such as ibuprofen, naproxen, benoxaprofen, flurbiprofen, ketoprofen, fenoprofen, fenbufen, ketorolac, sulfasalazine, indopropfen, pirprofen, carprofen, oxaprozin, pranoprofen, miroprofen, tioxaprofen, suprofen, alminoprofen, and tiaprofenic; or a pyrazole, such as phenylbutazone, oxyphenbutazone, feprazone, azapropazone, or trimethazone.

Unit Dose

As discussed above the volume of anti-inflammatory drug formulation injected is preferably in the range of from 0.1-2.0 mL to be suitable for the retroauricular injection. It is preferred to use a ready-to-use formulation, and accordingly, another aspect of the invention relates to a unit dose having a volume of from 0.1 to 2.0 mL of anti-inflammatory drug depot formulation. Accordingly, in some embodiments, a unit dose is provided of 0.1 to 2.0 mL of an anti-inflammatory drug depot formulation. In particular embodiments, the anti-inflammatory drug is a steroid. In some embodiments, the steroid is selected from the group of betamethasone, methylprednisolone, triamcinolonacetonide, and triamcinolonhexacetonide. In other embodiments, a unit dose is provided of 0.1 to 2.0 mL of an NSAID depot formulation.

The unit dose preferably comprises one of the dosages of steroid discussed above or a dosage equivalent therewith.

The concentration of steroids in the unit dose is preferably
7 mg/mL for betamethasone,
40 mg/mL for methylprednisolone,
40 mg/mL for triamcinolonacetonide,
20 mg/mL for triamcinolonhexacetonide.

In embodiments, where the anti-inflammatory drug is betamethasone, the drug is present in the depot formulation at a concentration in the range of 0.7 to 140 mg/mL, such as 0.8 to 100 mg/mL, such as 0.9 to 50 mg/mL, such as 1 to 35 mg/mL, such as 1.1 to 30 mg/mL, such as 1.2 to 28 mg/mL, such as 1.3 to 25 mg/mL, such as 1.4 to 22.5 mg/mL, such as 1.5 to 20 mg/mL, such as 1.6 to 17.5 mg/mL, such as 1.8 to 15 mg/mL, such as 2 to 14 mg/mL, such as 2.2 mg/mL to 13 mg/mL, such as 2.5 to 12 mg/mL, such as 2.8 to 11 mg/mL, such as 3 to 10 mg/mL, such as 4 to 9 mg/mL, such as 5 to 8 mg/mL, such as 6 to 7 mg/mL, such as 7 mg/mL. In some embodiments, the volume of the depot is 0.25 mL and the concentration of betamethasone is between 5.6 and 56 mg/mL, such as between 6 and 50 mg/mL, for example between 7 and 45 mg/mL, such as between 8 and 40 mg/mL, for example between 9 and 35 mg/mL, such as between 10 and 30 mg/mL, for example between 12 and 25 mg/mL, such as between 15 and 20 mg/mL. In other embodiments, the volume of the depot formulation is 0.5 mL and the concentration of betamethasone is between 2.8 and 28 mg/mL, such as between 3 and 25 mg/mL, for example between 4 and 20 mg/mL, such as between 5 and 15 mg/mL, for example between 6 and 10 mg/mL, such as between 7 and 9 mg/mL, for example 7 mg/mL or 8 mg/mL.

In other embodiments, the drug is methylprednisolone and is present in the depot formulation at a concentration in the range of 2 to 800 mg/mL, such as 2.1 to 400 mg/mL, such as 2.2 to 300 mg/mL, such as 2.4 to 275 mg/mL, such as 2.5 to 200 mg/mL, such as 2.7 to 150 mg/mL, such as 2.9 to 125 mg/mL, such as 3 to 110 mg/mL, such as 3.5 to 100 mg/mL, such as 4 to 90 mg/mL, such as 4.5 to 80 mg/mL, such as 5 to 75 mg/mL, such as 6 mg/mL to 70 mg/mL, such as 7 to 65 mg/mL, such as 8 to 60 mg/mL, such as 9 to 55 mg/mL, such as 8 to 50 mg/mL, such as 9 to 45 mg/mL, such as 10 to 40 mg/mL, such as 15 to 40 mg/mL, such as 20 to 40 mg/mL, such as 25 to 40 mg/mL, such as 30 to 40 mg/mL, such as 35 to 40 mg/mL, such as 40 mg/mL. In some embodiments, the volume is 0.25 mL and the concentration of methylprednisolone is between 16 and 320 mg/mL, such as between 17 and 300 mg/mL, for example between 18 and 275 mg/mL, such as between 19 and 250 mg/mL, for example between 20 and 225 mg/mL, such as between 25 and 200 mg/mL, for example between 30 and 175 mg/mL, such as between 40 and 150 mg/mL, for example between 50 and 125 mg/mL, such as between 75 and 100 mg/mL. In other embodiments, the volume is 0.5 mL and the concentration of methylprednisolone is between 8 and 160 mg/mL, such as between 9 and 140 mg/mL, for example between 10 and 120 mg/mL, such as between 15 and 100 mg/mL, for example between 20 and 90 mg/mL, such as between 30 and 80 mg/mL, for example between 40 and 70 mg/mL, for example between 50 and 60 mg/mL.

In other embodiments, the drug is triamcinolonacetonide and is present in the depot formulation at a concentration in the range of 5 to 800 mg/mL, such as 5.5 to 400 mg/mL, such as 6 to 300 mg/mL, such as 6.5 to 275 mg/mL, such as 7 to 200 mg/mL, such as 7.5 to 150 mg/mL, such as 8 to 125 mg/mL, such as 9 to 110 mg/mL, such as 10 to 100 mg/mL, such as 11 to 90 mg/mL, such as 12 to 80 mg/mL, such as 13 to 75 mg/mL, such as 14 mg/mL to 70 mg/mL, such as 15 to 65 mg/mL, such as 17.5 to 60 mg/mL, such as 20 to 55 mg/mL, such as 25 to 50 mg/mL, such as 30 to 45 mg/mL, such as 35 to 40 mg/mL, such as 40 mg/mL. In some embodiments, the volume is 0.25 mL and the concentration of triamcinolonacetonide is between 40 and 320 mg/mL, such as between 50 and 300 mg/mL, for example between 60 and 275 mg/mL, such as between 70 and 250 mg/mL, for example between 80 and 225 mg/mL, such as between 90 and 200 mg/mL, for example between 100 and 175 mg/mL, such as between 125 and 150 mg/mL. In other embodiments, the volume is 0.5 mL and the concentration of triamcinolonacetonide is between 20 and 160 mg/mL, such as between 30 and 140 mg/mL, for example between 40 and 120 mg/mL, such as between 50 and 100 mg/mL, for example between 60 and 80 mg/mL, such as 70 mg/mL.

In other embodiments, the drug is triamcinolonhexacetonide and is present in the depot formulation at a concentration in the range of 2.5 to 800 mg/mL, such as 3 to 400 mg/mL, such as 3.5 to 300 mg/mL, such as 4 to 275 mg/mL, such as 4.5 to 200 mg/mL, such as 5 to 150 mg/mL, such as 6 to 125 mg/mL, such as 7 to 110 mg/mL, such as 8 to 100 mg/mL, such as 9 to 90 mg/mL, such as 10 to 80 mg/mL, such as 12.5 to 75 mg/mL, such as 15 mg/mL to 70 mg/mL, such as 17.5 to 65 mg/mL, such as 20 to 60 mg/mL, such as 20 to 50 mg/mL, such as 20 to 40 mg/mL, such as 20 to 30 mg/mL, such as 20 to 25 mg/mL, such as 20 mg/mL. In some embodiments, the volume is 0.25 mL and the concentration of triamcinolonhexacetonide is between 20 and 160 mg/mL, such as between 30 and 140 mg/mL, for example between 40 and 120 mg/mL, such as between 50 and 100 mg/mL, for example between 60 and 80 mg/mL, such as 70 mg/mL. In other embodiments, the volume is 0.5 mL and the concentration of triamcinolonhexacetonide is between 10 and 80 mg/mL, such as between 15 and 75 mg/mL, for example between 20 and 70 mg/mL, such as between 25 and 65 mg/mL, for example between 30 and 60 mg/mL, such as between 35 and 55 mg/mL, for example between 40 and 50 mg/mL, such as 55 mg/mL.

The present anti-inflammatory drugs may be administered in dosages that are such that the drug is therapeutically active over the desired period of time.

In some embodiments, the drug is betamethasone and the dosage is between 1 and 10 mg, such as between 1.5 and 9 mg, such as between 2 and 8 mg, such as between 2.5 and 7 mg, such as between 3 and 6 mg, such as between 3.5 and 5 mg, such as 4 mg.

In other embodiments, the drug is methylprednisolone and the dosage is between 1 and 50 mg, such as between 5 and 40 mg, such as between 10 and 30 mg, such as between 15 and 25 mg, such as between 16 and 24 mg, such as between 17 and 23 mg, such as between 18 and 22 mg, such as between 19 and 21 mg, such as 20 mg.

In other embodiments, the drug is triamcinolonacetonide and the dosage is between 1 and 50 mg, such as between 5 and 40 mg, such as between 10 and 30 mg, such as between 15 and 25 mg, such as between 16 and 24 mg, such as between 17 and 23 mg, such as between 18 and 22 mg, such as between 19 and 21 mg, such as 20 mg.

In other embodiments, the drug is triamcinolonhexacetonide and the dosage is between 1 and 20 mg, such as between 1.5 and 19 mg, such as between 2 and 18 mg, such as between 3 and 17 mg, such as between 4 and 16 mg, such as between 5 and 15 mg, such as between 6 and 14 mg, such as between 7 and 13 mg, such as between 8 and 12 mg, such as between 9 and 11 mg, such as 10 mg.

For other steroids the dosages are calculated as equivalents of the above dosages.

Examples

Clinical Investigations

The pressure inside the ME cavity is normally equal to the ambient pressure, but in many ME diseases the formation of underpressure plays an important role. Thus, in the physiology of the ME, the understanding of its pressure regulation is overwhelmingly important, though it has not been fully clarified.

We have performed physiological studies investigating the regulation of the ME pressure following experimentally induced pressure changes within the ME. This study has shown that there are two different mechanisms for counter-regulation of the induced pressure changes: 1) the well-known opening of the Eustachian tube with fast stepwise pressure changes against ambient pressure, and 2) unknown slower gradual changes, which may cross the ambient baseline and continue from positive to negative pressures and vice versa.

Figure 2:
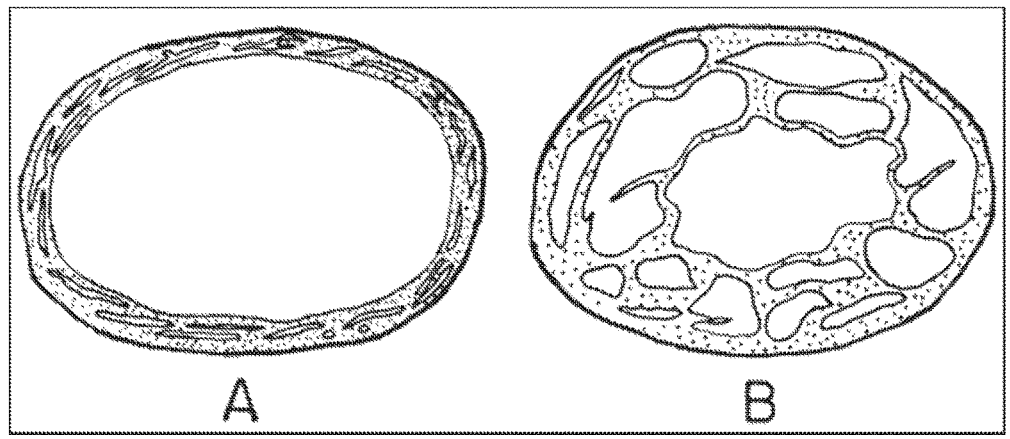
FIG. 2. (A) The normal mucosa with a lower blood content; (B) The blood vessels are filled with blood (congestion), and thus, the mucosa expands; this causes a compression of the air volume and an increased air pressure. The opposite effect with a decrease of the vascular content of blood (decongestion) will lead to an expansion of the air volume, and thus, a decreased air pressure.

The only way these gradual pressure changes can be explained is that the ME mucosa gradually changes its volume based on concurrent changes in its blood congestion. If the volume of the mucosa increases in a closed air filled cavity, the air pressure is increased, and vice versa (FIG. 2). Moreover, it seems obvious that changes in the thickness of the very large area of the mastoid mucosa can be particularly efficient in its influence on the ME pressure; thus, it has been calculated that a change of 6 µm in mucosa thickness can induce a pressure change of 1 kPa in a normal adult ME cavity. This mechanism is known in diving mammals, which need a very effective pressure regulation, when they dive at more 100's meters of depth. Moreover, the same basic mechanism is known from the human nasal mucosa, which by its congestion and volume changes can regulate the air flow through the nasal cavities.

Structural Investigations

Figure 3:
FIG. 3. Normal human mastoid mucosa (40×); immunostaining with CD31, which stains the endothelium inside the blood vessels; there can be seen numerous blood vessels with thin walls (veins), situated very close to each other (sinusoids). The connective tissue is loose with few collagen fibres.
Figure 4:
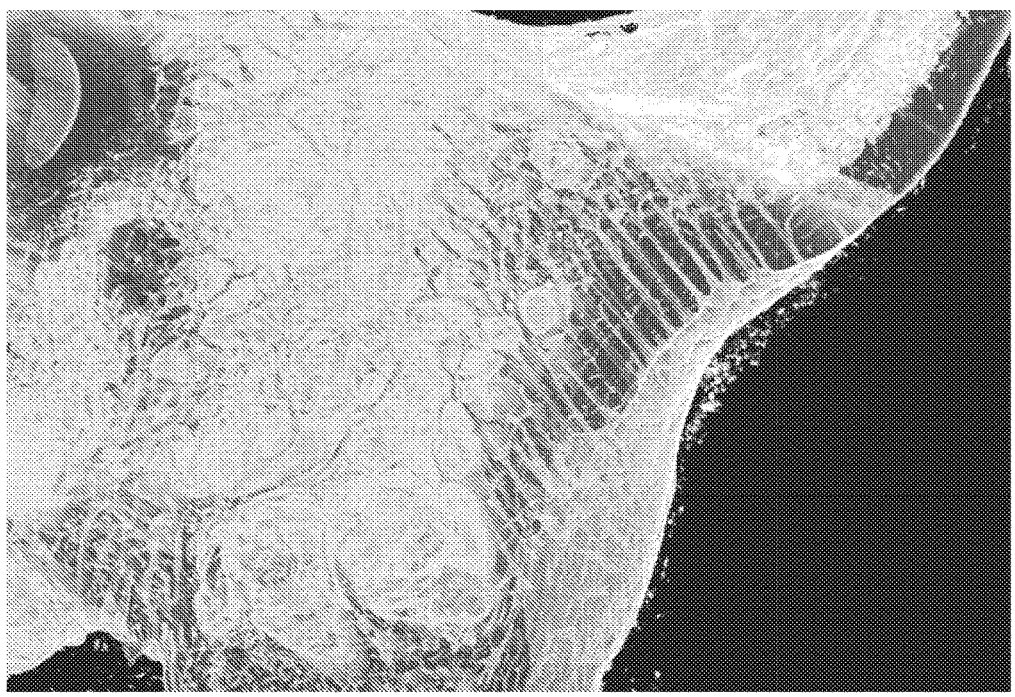
FIG. 4. Micro-CT scanning with numerous microchannels, which connect the bone surface behind the outer ear with the deep mastoid structure. The black areas crossed by the microchannels are the compact part of the mastoid bone.

Consequently, our further research has focused on the mastoid structure both by micro-CT scanning and histological studies. Histological investigations have confirmed that the mucosa has very loose subepithelial connective tissue with few collagen fibres and a rich vascular supply—these two basic characteristics are essential for the mechanism of changes in congestion and mucosa volume. We have also preliminarily shown a certain occurrence of sinusoid veins, which are possibly arranged in smaller formations like "corpuscles" (FIG. 3). These structures resemble those of the nasal mucosa with an essential role in nasal physiology discussed above. It is therefore highly likely that similar structures may be found in the mastoid mucosa, which is also part of the upper airways—the entity named the "united airways"—though sinusoids have not earlier been described in the ME.

Further, we have investigated the structure of the ME with micro-CT scanning. These studies have revealed numerous micro-channels between the surface of the mastoid bone behind the outer ear and the mastoid air cells deep inside the mastoid; these channels have also not been described earlier, since they cannot be demonstrated by clinical CT-scanning, because they are only 150 µm in diameter. We have also shown that these micro-channels contain blood vessels, and so they constitute a very rich blood supply for the mastoid mucosa.

When the postnatal pneumatization process mentioned earlier is taken into consideration, where mastoid cells are formed by expansion from the tympanum, and where the mucosa and the blood supply is likely to follow this expansion, the vascular supply formed by the microchannels seem to play a role as an additional blood supply.

Recurrent or chronic inflammation invariably leads to fibrosis of the tissue, and if the function of the mastoid mucosa including sinusoids depend on a loose connective tissue, then fibrosis may limit the function. Thus, the immediate effects of anti-inflammatory drugs on secretory otitis media (relieve of ear pressure sensation, middle ear effusion and decreased hearing) may also be accompanied by long-term benefits by limiting any fibrotic changes of the mucosa.

Treatment of Otitis Media

1) A 4 years old child suffering from recurrent secretory otitis media on the left ear is referred to the clinic. 0.25 mL of betamethasone depot formulation corresponding to 4 mg betamethasone is subcutaneously injected into the left retroauricular fold. Within a few days the effect of the treatment is felt by the patient and measureable by tympanometry.
2) A 25 years old male suffering from acute secretory otitis media on the right ear is referred to the clinic. 0.5 mL of a methylprednisolone depot formulation corresponding to 20 mg methylprednisolone is subcutaneously injected into the right retroauricular fold. Within a week the effect of the treatment is felt by the patient and measureable by tympanometry.

REFERENCES

Hanusdorf, 2001, J Interv Cardiol. 2001 February; 14 (1): 69-76
Langer et al., 1981, J. Biomed. Mater. Res. 15:167-277
Langer, 1982, Chem. Tech. 12:98-105
Sidman et al., 1983, Biopolymers 22:547-556
U.S. Pat. No. 5,245,098 (Summers et al.)
WO 2005/013936 (Sheng-Hung et al.)

The invention claimed is:

1. A method of treatment of otitis media in an individual in need thereof, comprising the step of injecting said individual with a retroauricular injection of a depot formulation of an anti-inflammatory drug.

2. The method according to claim 1, wherein the otitis media is secretory otitis media.

3. The method according to claim 1, wherein the anti-inflammatory drug is a steroid or an NSAID.

4. The method according to claim 3, wherein the steroid is selected from the group of betamethasone, methylprednisolone, triamcinolonacetonide, and triamcinolonhexacetonide.

5. The method according to claim 3, wherein the anti-inflammatory drug is an NSAID.

6. The method according to claim 1, wherein the volume of the depot formulation is in the range of from 0.1-2.0 mL.

7. The method according to claim 1, wherein the depot formulation further comprises a second anti-inflammatory drug.

8. The method according to claim 1, wherein the depot formulation further comprises an antibiotic.

9. The method according to claim 1, wherein the depot formulation allows sustained release of the antiinflammatory drug over a period of time.

* * * * *